United States Patent [19]
Ferk et al.

[11] Patent Number: 5,105,041
[45] Date of Patent: * Apr. 14, 1992

[54] EFFLUENT SEPARATION METHOD FOR AROMATIC HYDROCARBON ALKYLATION PROCESS

[75] Inventors: Don L. Ferk, Hampton, Va.; Eugene Schmelzer, Skokie; Edward C. Haun, Glendale Heights, both of Ill.

[73] Assignee: UOP, Des Plaines, Ill.

[*] Notice: The portion of the term of this patent subsequent to Dec. 5, 2006 has been disclaimed.

[21] Appl. No.: 582,813

[22] Filed: Sep. 10, 1990

Related U.S. Application Data

[63] Continuation of Ser. No. 422,280, Oct. 16, 1989, abandoned, which is a continuation-in-part of Ser. No. 152,204, Feb. 5, 1988, Pat. No. 4,885,424.

[51] Int. Cl.$^5$ .................................. C07C 2/64
[52] U.S. Cl. .................................. 585/450; 585/446; 585/804; 585/802; 208/361; 208/364; 208/365; 208/362; 208/350; 208/351; 208/355
[58] Field of Search ............... 585/450, 446, 470, 804, 585/802; 208/351, 361, 364, 365, 362, 350, 355

[56] References Cited

U.S. PATENT DOCUMENTS

| | | | |
|---|---|---|---|
| 4,587,370 | 5/1986 | DeGraff | 585/446 |
| 4,695,665 | 9/1987 | DeGraff | 585/450 |
| 4,885,424 | 12/1989 | Ferk et al. | 585/450 |

OTHER PUBLICATIONS

Danfield et al, "Improving Cumem Yield Via Selective Catalysis," Chem. Eng. Mar. 21, 1983 edition, pp. 32–33.

*Primary Examiner*—Helane E. Myers
*Attorney, Agent, or Firm*—Thomas K. McBride; John G. Tolomei

[57] ABSTRACT

A process for the production of alkylaromatic hydrocarbons uses a working fluid to reduce the costs of separating an unreacted aromatic feed substrate from aromatic hydrocarbon products. Unreacted aromatic substrate is combined with a light hydrocarbon, such as propane, to form a combined effluent stream. The combined effluent stream enters a flash separator where unreacted aromatic substrate is lifted overhead with the light hydrocarbon while heavier aromatic products are recovered below. The aromatic substrate and light hydrocarbon are easily separated in a simple separation zone. Lifting the aromatic substrate with the working fluid reduces the volume of aromatic substrate that remains with the aromatic product so that the more energy intensive separation of the aromatic substrate and aromatic product is performed on a reduced volume of material.

2 Claims, 1 Drawing Sheet

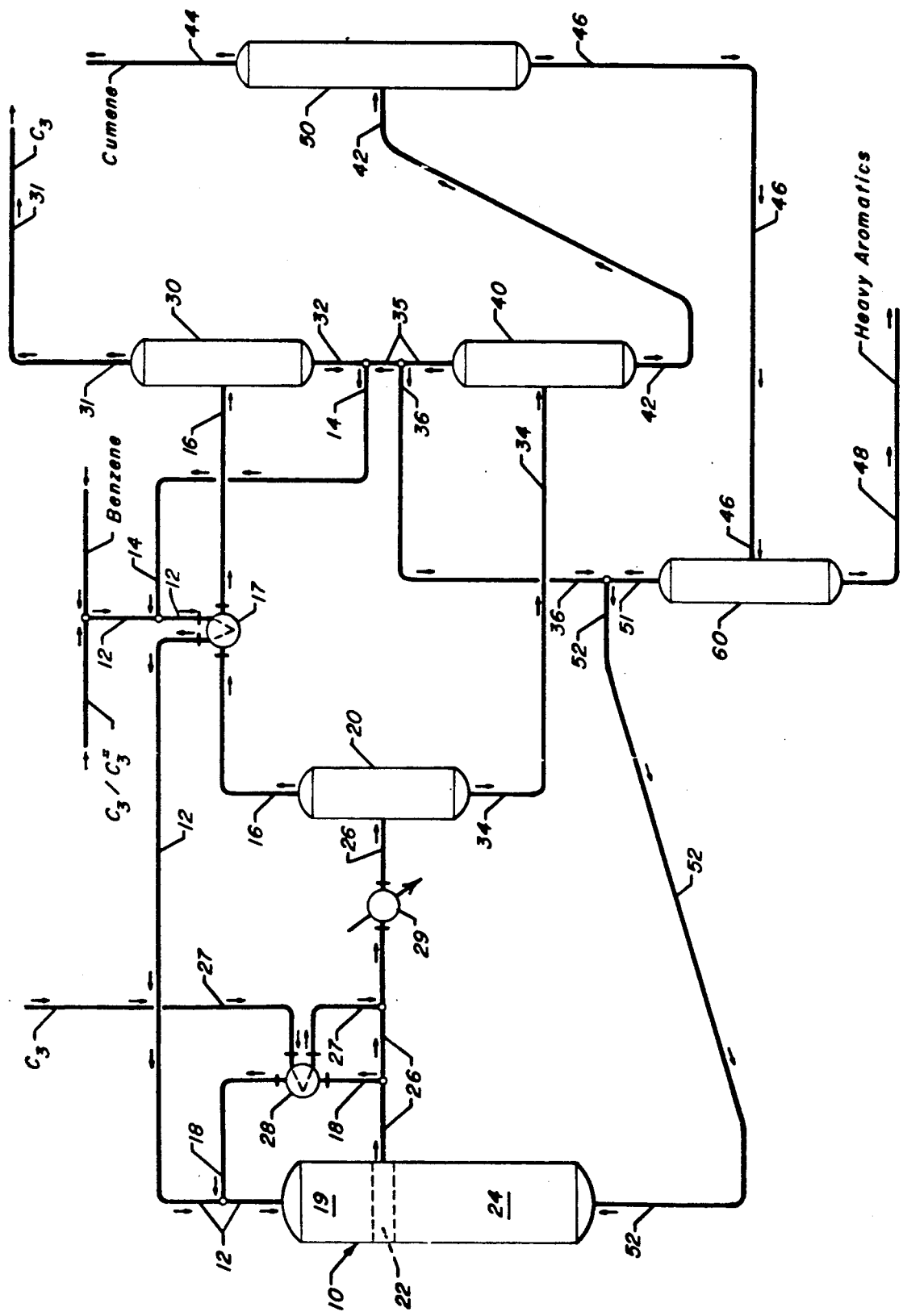

EFFLUENT SEPARATION METHOD FOR AROMATIC HYDROCARBON ALKYLATION PROCESS

REFERENCE TO PRIOR APPLICATIONS

This application is a continuation of Ser. No. 422,280 filed Oct. 16, 1989 that was allowed on Aug. 15, 1990 and abandoned after the filing of this application and which was a continuation-in-part of Ser. No. 152,204 filed Feb. 5, 1988 that issued on Dec. 5, 1989 as U.S. Pat. No. 4,885,424.

FIELD OF THE INVENTION

The invention relates to a hydrocarbon conversion process. The invention more specifically relates to the production of alkylaromatic hydrocarbons by the reaction of an acyclic olefinic hydrocarbon with an aromatic feed hydrocarbon.

PRIOR ART

The alkylation of aromatic hydrocarbons such as benzene using solid catalysts is a well-developed art which is practiced commercially in large scale industrial units. One commercial application of this process is the alkylation of benzene with propylene to form cumene (isopropylbenzene), which is subsequently used in the production of phenol and acetone. Those skilled in the art are therefore familiar with the general design and operation of such alkylation process.

The prior art is well described in the literature. For instance, a typical flow scheme suitable for commercial use is depicted in U.S. Pat. No. 4,051,191 issued to D. J. Ward. This reference describes in some detail, catalyst, reaction conditions, and separatory methods suitable for the recovery of cumene. The reactor effluent is passed into a rectification zone in which propane, charged to the process in admixture with the feed propylene, is separated for recycling and for rejection from the process. Liquid phase hydrocarbons recovered in the rectification zone are then passed into a two-column fractionation train comprising a recycle column and a cumene or product column. The benzene feed aromatic hydrocarbon is recycled from the top of the first fractionation column. The product cumene is recovered from the top of the second fractionation column, with heavy aromatic by-products being withdrawn bottom of the second column.

U.S. Pat. Nos. 4,695,665 and 4,578,370 issued to R. R. DeGraff are also directed to the separation of products and the recovery of recycle streams from processes for the alkylation of aromatic hydrocarbons. U.S. Pat. No. 4,695,665 discloses the use of flash drum that receives the overhead from an effluent rectifier.

U.S. Pat. No. 3,437,708 issued to J. E. Gantt shows the use of a flash tower for the initial separation of an alkylaromatic or oligomerization zone product stream. The flash zone is used to recover a vapor stream and first and second liquid streams.

Another product recovery fractionation train for commercial use is described in the article at page 32 of the Mar. 21, 1983 edition of Chemical Engineering magazine. This system employs four fractionation columns in series. The first fractionation column is a depropanizer column. The third column is a product column in which cumene is removed as the net overhead product. The net bottoms stream of the product column is passed into a recycle column with the overhead stream of this column apparently being recycled to the reaction zone. The alkylation process described in this article is based upon the use of an aluminum chloride catalyst system as compared to the solid phosphoric acid-type catalyst which is preferred in the previously cited reference.

A number of methods are known to enhance the efficiency of separating mixtures containing aromatic hydrocarbons. It is known in the art of fractional distillation that the latent heat present in the overhead vapors of one fractionation column may be employed in the reboiler means of another fractionation column for the purpose of supplying heat to the other fractionation column. This is shown for instance in U.S. Pat. No. 3,254,024 issued to H. A. Huckins, Jr. et al. The Huckin's reference is directed to the separation of $C_8$ aromatic hydrocarbons wherein overhead vapor from a xylene splitter column is used to reboil an ethylbenzene column. U.S. Pat. No. 4,360,405 issued to U. Tsao is pertinent for its showing a fractionation arrangement for use in the separation of close boiling mixtures in which the overhead vapor of one column is compressed and passed into a bottom portion of an immediately upstream fractionation column. The bottoms liquid from this upstream column flows into the top of the downstream column. This reference indicates this arrangement could be employed for the separation of aromatic hydrocarbons exemplified by the xylenes.

BRIEF SUMMARY OF THE INVENTION

Briefly stated the invention is the addition of a working stream having a high energy content to a product stream comprising aromatic hydrocarbons in order to reduce the cost of separating recycled aromatic components from the product stream. The working stream has a boiling point which is substantially lower than the aromatic hydrocarbons and low enough to vaporize the working stream at the temperature of process streams containing unutilized or waste heat. The product stream and working stream enter a flash separator where the working stream lifts a substantial portion of an aromatic hydrocarbon from the product stream. The working stream and the lifted aromatic hydrocarbons make up the flash separator overhead stream. This overhead stream enters a separation zone where the working stream and the aromatic hydrocarbons are split. In this manner, the working stream absorbs relatively low level heat from the process and concentrates the heat so that it becomes a high enthalpy vapor that is used to reduce the external heat requirements of the process.

In a more specific aspect of this invention, the product stream comprises the effluent of a reaction zone and includes unreacted aromatic hydrocarbon feed and relatively higher boiling aromatic product hydrocarbons and by-products. After passage through the flash separator and recovery in the separation zone, the feed aromatic hydrocarbons are recycled to the reaction zone while the working stream is either removed from the process or recycled to the effluent of the reaction zone to facilitate separation of the feed hydrocarbons from the product hydrocarbons. This arrangement promotes efficiency by lifting a portion of the aromatic hydrocarbon feed in the flash separator and allowing a substantial portion of the feed hydrocarbons to be carried with the working fluid to the separation zone in which the aromatic hydrocarbon feed and the working fluid are easily split due to their relative boiling point difference. Therefore, the overall amount of feed and product aromatic hydrocarbons that must be separated in the fractionation column using external heat input is reduced by separating a portion of these hydrocarbons with waste heat from the process in the flash separator. This arrangement is particularly advantageous when the working fluid is normally present in the feed to the reaction zone so that separation facilities for removing the working fluid are usually present. In such cases, the only cost associated with the recycling of the working fluid is the cost of a pump and relatively minor increases in flash separator facilities and utilities.

In a more limited embodiment of this invention, a feed aromatic hydrocarbon and an acyclic hydrocarbon are alkylated at alkylation conditions in an alkylation reaction zone to provide a reaction zone effluent that includes unconverted feed aromatic hydrocarbons, product aromatic hydrocarbons and hydrocarbon by-products. By the method of this invention, at least a portion of the aromatic hydrocarbon feed is recovered by combining the reaction zone effluent with a working fluid having a substantially lower boiling point than the aromatic hydrocarbon feed. The combined effluent stream is maintained at conditions suitable to keep most of the working fluid in the vapor phase. The combined effluent passes to a flash separator from which an overhead stream containing the working fluid and at least a portion of the aromatic hydrocarbon feed is recovered. The overhead stream from the flash separator passes to a separation zone from which a recycle stream comprising the aromatic hydrocarbon feed and a working fluid comprising low boiling hydrocarbons are recovered. At least a portion of the recycle stream is returned to the alkylation zone and at least a portion of the working fluid is combined with the reactor effluent stream.

BRIEF DESCRIPTION OF THE DRAWING

A more specific aspect of this invention resides in the flow scheme of the attached drawing. The drawing shows a reactor 10 for alkylating and transalkylating acyclic and aromatic hydrocarbons and a flash separator 20 for receiving the effluent from reactor 10. An overhead stream from separator 20 containing unreacted aromatic hydrocarbons and a working fluid enter a separator 30 which provides an overhead stream containing low boiling hydrocarbons and a bottoms stream containing unreacted aromatic hydrocarbon. The bottoms stream from flash separator 20 enters a recycle column 40 which provides an overhead stream of unreacted aromatic hydrocarbon and light hydrocarbon by-products and a bottoms stream containing product alkylate and other heavy aromatic by-products. The bottoms stream from recycle column 40 enters product column 50 from which product is recovered overhead and a bottoms stream containing heavy aromatic hydrocarbons enters a heavy alkylate column 60. Column 60 removes transalkylatable hydrocarbons as an overhead stream which are returned to reactor 10 and rejects heavier hydrocarbon material through the bottoms stream.

DETAILED DESCRIPTION OF THE INVENTION

The principal object of this invention is to decrease the cost of recovering alkylatable aromatic hydrocarbons from the effluent of a reaction zone for the alkylation of aromatic hydrocarbons by increasing the internal heat utilization of the process. Accordingly, this invention centers around the separation of the effluent stream and the method of operating a recovery section to separate the effluent into products, recycle material, and rejected components. Applicable effluent streams are those from an aromatic alkylation zone where an aromatic substrate and an acyclic alkylation agent are alkylated to yield at least one alkylate product having a boiling point that is higher than the boiling point of either the aromatic substrate or one of the alkylated aromatic products. The most benefit is obtained from the invention when the hydrocarbons of the effluent are primarily in a liquid phase.

According to this invention, the effluent stream is admixed with a working fluid that aids in the separation of the aromatic substrate from the aromatic reaction products. The working fluid can be any condensible fluid having a substantially lower boiling point than that of the aromatic substrate. Preferably, the working fluid comprises acyclic hydrocarbons having a boiling point difference of at least 60° C. with the aromatic substrate. Hydrocarbons for the working fluid are preferably light hydrocarbons composed of $C_4$ or lower carbon number paraffins and more preferably, $C_3$ paraffins. Normally, the addition rate of the working fluid is equal to 2-20% of the net effluent mass flow rate. Essentially all of the working fluid will be in a vapor phase before it is combined with the effluent stream. The working fluid is vaporized by heat exchange with one or more process streams. Therefore, a suitable working fluid must be able to extract heat from one or more process streams at temperature levels that will vaporize the working fluid or preferably super heat the working fluid. In addition, the working fluid must be easily separated from the aromatic substrate. It is also desired to recycle the working fluid as a pumpable liquid; therefore, the working fluid is preferable condensable at ordinary process pressure levels without refrigeration.

The combined effluent and working fluid enter a flash separator at a temperature sufficient to maintain a majority of the working fluid and a portion of the effluent in the vapor phase. This temperature is less than the boiling point of the aromatic substrate. The combined effluent and working fluid may be brought to a suitable temperature by external heating of the separation hydrocarbon, heating of the combined effluent stream, heat addition to the flash separator or a combination of the foregoing methods. The flash separator is maintained at temperature equal to or near the temperature of the aromatic substrate, such that the separation hydrocarbon will be primarily in the vapor phase and travel upward in the flash separator zone while essentially all the heavier aromatic reaction products will fall to the bottom of the flash separator. Since the working fluid is above its boiling point at the conditions of the flash separator, a portion of the lighter aromatic hydrocarbons will be vaporized so that the rising working fluid will lift the aromatic substrate to the top of the flash separator. In this manner, the flash separator performs a rough split of the aromatic substrate between an overhead fraction which is relatively free of aromatic alkylation product and a bottom fraction which is relatively free of working fluid hydrocarbons. The working fluid serves dual purposes of supplying internal heat from the process to lift a proportionately greater amount of aromatic substrate while at the same time acting as a diluent or stripping medium to lower the flash temperature of the effluent mixture in the flash separator.

The flash separator is simple in design and may consist of a single vessel having an open interior. If desired, the flash separator may contain internals such as sieve trays, valve trays or packing. When boiling points are close, a small amount of reflux may be included to enhance the separation between the aromatic substrate and the aromatic alkylate product. The only major control variable for the flash separator is its temperature. By adjusting this temperature and the working fluid flow rate, it is possible to vary the quantity of aromatic substrate entering either the upper or lower effluents within a range of about 10%-70% of the total aromatic substrate entering the flash separator. In the case of a $C_3$ hydrocarbon, working fluid and a benzene substrate, the flash separator is operated such that the effluent from the flash separator has a temperature of less than 205° C. (400° F.) and more preferably less than 190° C. (370° F.). The simple construction of the separator and the relatively easy means of operation makes the flash separator a relatively inexpensive adjunct to the recovery process.

The bottom stream from the flash separator will enter additional separation facilities to perform the more complete separation of the aromatic substrate and light hydrocarbon by-products from the aromatic alkylation product. Thus, energy usage in the subsequent separation stage is reduced proportionally by the amount of the aromatic substrate recovered in the rectification zone. Small amounts of light hydrocarbon by-products or working fluid hydrocarbons that are carried over with the bottoms stream are also received with the aromatic substrate.

The upper stream from the flash separator, containing the aromatic substrate, the working fluid and in some cases a small amount of alkylation product is partially condensed for heat recovery purposes and then transferred to another separation zone. The desired degree of separation between the aromatic substrate and the working fluid is readily accomplished in the next separation zone due to the difference in boiling points between the two compounds. The working fluid is principally recovered as an upper or overhead stream. The working fluid may be withdrawn or at least a portion of it recycled again to the reaction zone effluent to perform the lift function as previously described. Most of the aromatic substrate leaves the separation zone in a bottoms stream. At least a portion of the bottoms stream is recycled to the reaction zone. The separator may be operated to obtain a desired exclusion of working fluid from the bottoms stream containing the aromatic substrate.

As stated, this invention comprises passing an alkylating agent and an aromatic substrate to an alkylation reaction zone to obtain an alkylated aromatic product. Thus, this invention can be applied to a wide variety of aromatic alkylation operations. The aromatic substrate for this invention may be benzene or an alkyl substituted benzene. Examples of such substrates include benzene, toluene, xylene, and ethyl benzene. A wide range of alkylating agents may be used in the alkylation reaction zone and include monoolefins, diolefins, polyolefins, acetylenic hydrocarbons, alkyl halides, alcohols, ethers, and esters. The preferred alkylation agent comprises monoolefinic hydrocarbons.

More specifically, it is preferred that the monoolefin is propylene. A highly advantageous embodiment of this invention uses a propane/propylene stream to supply a propylene alkylating agent and recovers propane as the working fluid. Since propane is normally present in the feed components, its use as the working fluid requires no additional facilities for recovery, recycle or makeup considerations.

The alkylation reactor of this invention will include at least one zone for alkylation of the substrate by the alkylation agent. Greatest advantage is obtained by the method of this invention when the alkylation reaction zone operates at relatively low temperature and at liquid phase conditions. These conditions include a temperature of from 150° C. to about 210° C. The alkylation zone should be operated to obtain an essentially complete conversion of the alkylating agent. To achieve this effect, additional aromatic substrate will usually be charged to the reaction zone. In a preferred form of this invention, the reaction zone contains an amorphous silica aluminum catalyst that is used for the alkylation of propylene and benzene. The preferred catalyst will be a cogelled silica aluminum composite which comprises from about 40 to 99 wt. % silica and from about 1 to about 60 wt. % alumina. The feed admixtures are introduced into reaction zone at a constant rate and in a molar ratio of about 1:1 to 20:1 aromatic substrate to olefinic alkylating agent with a ratio of about 2:1 to 6:1 being preferred. These include solid phosphoric acid catalyst, aluminum chloride catalyst, and amorphous silica alumina catalyst.

A wide range of operating conditions are used in the alkylation of aromatic hydrocarbons. Temperatures range from 100° C. to about 390° C. the range of 150° C. to about 275° C. being preferred when used in conjunction with the preferred amorphous silica alumina catalyst. Pressures can also vary within a range of about 1 atmosphere to 130 atmospheres. Generally, the pressure should be sufficient to maintain the reactants in a liquid phase and will fall in a range from about 10 to 40 atmospheres. Reactants are generally passed through the alkylation zone at a mass flow rate sufficient to yield a liquid hourly space velocity (LHSV) of from about 0.5 to 50 hrs.$^{-1}$ and especially from about 2 to 10 hrs.$^{-1}$.

In alkylating the aromatic substrate with the alkylating agent, a substantial quantity of polyalkylated aromatic compounds may also be formed, particularly when using the preferred catalyst, lower operating temperatures and lower aromatic substrate to olefinic alkylating agent ratios. Therefore, it is common practice for the reactor to include an additional transalkylation zone for monoalkylated hydrocarbons are the desired product. A highly desirable form of reactor has an upper catalyst bed which provides an alkylation zone for incoming aromatic substrate and alkylation agent and a lower transalkylation zone that receives polyalkyl aromatic compounds and additional aromatic substrate. In a preferred form reactants and products pass downwardly through the alkylation zone and upwardly through the transalkylation zone and are combined at a common central point in the reactor to provide an effluent stream containing aromatic substrate, monoalkylated product, and polyalkylated compounds that are subsequently separated to provide aromatic substrate for return to the alkylation and transalkylation zone, a monoalkylated product stream and a stream of polyalkylated hydrocarbons for feed to the transalkylation zone. A wide variety of transalkylation catalysts can be used in the transalkylation zone. These catalysts include Friedel-Crafts catalysts such as sulfuric acid, phosphoric acid and aluminum chloride. A preferred catalyst is an acid-washed crystalline alumina silicate material and a refractory inorganic oxide material with the composite having an average pore diameter of 6 angstroms or greater and a surface area of 590 m$^2$/g or greater. A particularly useful form of crystalline alumina silicate material for the transalkylation catalyst is a hydrogen form silica alumina having either a three-dimensional or channel pore structure crystal lattice framework. A particularly preferred channel pore crystalline alumina silicate is mordenite. The preferred inorganic oxide for use in the transalkylation catalyst is alumina with gamma-alumina, eta-alumina, and mixtures thereof being particularly preferred. The hydrogen form alumina silicate may be present in a range of from 5 to 99.5 wt. % and the refractory inorganic oxide may be present in a range of from 0.5 to 95 wt. %. A transalkylation reaction can be carried out in a broad range of operating conditions including temperatures from 100° C. (210° F.) to about 390° C. (735° F.) and pressures ranging from 1 atmosphere to about 130 atmospheres. The pressure will generally be selected such that the reactants will remain in the liquid phase and will, therefore, be from about 10 to about 40 atmospheres. A liquid hourly space velocity based on the combined aromatic substrate and poly or alkyl aromatic feed rate from about 0.1 to 50 hrs.$^{-1}$ is desirable. A more desirable range of LHSV is from 0.5 to 5 hrs.$^{-1}$.

This invention will be further described in the context of a preferred embodiment which is the alkylation of propylene with benzene to obtain cumene. The description of this invention, in terms of a preferred embodiment, is not meant to limit the claims of this invention to the particular details disclosed herein. The flow scheme for this example is that shown in FIG. 1. This example is based on engineering calculations and actual operating experience with similar processes. In describing this example, valves, pumps, heaters, instruments, and heat exchangers other than those necessary for an understanding and appreciation of the invention have been omitted. The feed to the process consists of benzene and a mixture of propane and propylene. The C$_3$ portion of the feed admixture will consist primarily of propylene in an amount from 60-80 wt. % propylene. The feed admixture flows through a line 12 where it is admixed with the contents of line 14 which comprise a benzene recycle stream obtained in a manner hereinafter described. Benzene is added to the feed admixture in order to increase the total concentration of benzene rings relative to propylene such that the benzene to propylene ratio is between 1:1 to 8:1 with a ratio between 2:1 and 6:1 being preferred. The feed components are exchanged in exchanger 17 against a hereinafter described flash separator overhead stream, carried by line 16, to raise its temperature to 150°-190° C. Line 18 carries a hereinafter described effluent recycle stream which is combined with the contents of line 12. The effluent recycle stream further increases the concentration of benzene rings to propylene alkylating agent to a ratio of from 3:1 to 15:1. Line 12 discharges the feed components into an alkylation reaction zone 19.

The alkylation reaction zone contains an amorphous silica alumina catalyst of the preferred type hereinbefore described. Contact of the feed components with the catalyst will result in an essentially complete conversion of propylene into cumene (isopropyl benzene), up to 30 wt. % of di-isopropyl benzene, trace amounts of tri-isopropyl benzene, lesser amounts of propylene condensation products such as hexene, nonene, etc., condensed benzene ring derivatives such as biphenyls and other heavy alkylate products that include hexyl and nonyl benzenes. Since the alkylation reaction is highly exothermic, a temperature rise of approximately 30° C. is held through the alkylation zone by adjusting the flow and heat removal rates of the effluent recycle. Reactants and products from the alkylation zone flow downwardly where they are combined in a collection zone 22 with upflowing reaction products and reactants from a transalkylation zone 24. The products and reactants from zone 24 include benzene, isopropyl benzene, and di- and tri-propyl benzenes plus minor amounts of other heavy alkylate components.

Line 26 collects the reaction products of the alkylation and transalkylation zones in an effluent at a temperature of about 180°-220° C. Between 35-75% of the effluent stream is taken by line 18 and exchanged against a hereinafter described working fluid stream 27 in an exchanger 28. Passage through exchanger 28 lowers the temperature of the effluent recycle material in line 18 to about 165°-205° C. as it imparts some of the heat of reaction from the alkylation zone to the contents of line 27.

Line 27 contains C$_3$'s, predominantly propane. The propane for line 27 may be externally supplied or taken from a hereinafter described separator 30. The contents of line 27 are combined with the net effluent from the reaction zone in line 26 to introduce the working fluid. Passage through heat exchanger 28 will provide a majority of the heat necessary for vaporization and possible superheating of the C$_3$'s before they are added to the contents of line 26. The combined recycle stream and effluent stream should be kept at a temperature sufficient to maintain a substantial quantity of the benzene in a vaporized state. Any additional heat required for this purpose is added by exchanger 29. The combined stream enters flash separator 20 at a temperature of from 155°-200° C. and a pressure of 13-17 atmospheres. Flash separator 20 is a simple disengaging vessel with a substantially open interior. The mixed phase components enter in the center of the vessel. The thermal equilibrium in the vessel is such that substantially all of the C$_3$'s and a significant portion of the benzene are in the vapor phase while substantially all of the alkyl aromatic products and the rest of the benzene are in the liquid phase, thereby effecting a relatively inexpensive separation of at least a portion of the benzene from the alkyl aromatic products contained in the effluent. Flash separator 20 can be operated to recover between 10-70% of the benzene from the net reactor effluent. The benzene and substantially all the C$_3$'s are collected overhead in line 16. The flash separator overhead of line 16 is cooled in exchanger 17 to a temperature of about 145°-70° C. This cooling condenses benzene and a portion of the propane prior to entering separator 30.

In separator 30, a relatively simple split between C$_3$'s and benzene is performed at a low energy cost. C$_3$'s, primarily propane, are recovered overhead from separator 30 to an overhead line 31. The working fluid can be withdrawn from line 31 as hereinbefore described. Net C$_3$'s and any lighter hydrocarbons that enter with the feed are recovered from line 31 and removed from the process. When the working fluid is taken from line 31, adjusting the net recovery through line 31 will maintain the working fluid volume at desired levels. A benzene bottom stream containing a relatively small amount of propane leaves separator 30 through line 32 and provides a portion of the recycled benzene that is added to the feed components by line 14. The separator is operated to minimize benzene in the overhead and allows a small quantity of $C_3$'s, less than about 15% in the bottom stream of line 14. Limiting the amount of $C_3$'s and lighter hydrocarbons to the reaction zone prevents vaporization of the combined reactor feed at the reactor operating conditions.

Benzene and higher boiling hydrocarbons are taken by a bottom line 34 from the lower section of flash separator 20 and transferred to a recycle fractionation column 40. The flash separator bottoms stream has a temperature of from 155°-200° C. Column 40 is a trayed column designed to perform a good split between the desired product cumene and the other lower boiling effluent components. As hereinabove mentioned, the net products from the reactor section will contain small quantities of propylene condensation products such as hexene and nonene. These components must be separated from the alkyl aromatic product at this point in the flow scheme, otherwise they will detrimentally contaminate the final cumene product. Thus, the overhead of column 40 typically has a small quantity of cumene in it. This amount may equal approximately 2.5 wt. % of the overhead based on benzene. Taking cumene overhead ensures that nonene, which has a boiling point of about 5° C. lower that cumene is carried overhead with the benzene. The contaminants make up a relatively small percentage of the overhead which consists primarily of benzene. Thus, this invention confers substantial heat savings on the operation of column 40 by reducing the amount of benzene that must be vaporized therein in direct proportion to the amount of benzene removed by flash separator 20. A portion of the overhead from line 35 is withdrawn by line 36 to supply benzene to transalkylation zone 24. The amount of overhead withdrawn by line 36 is on the order of one-half. The remainder of the overhead taken by line 35 is mixed with benzene from line 32 to make up the remainder of the benzene recycle of line 14.

Line 42 transfers the heavier effluent components from column 40 to a product fractionation column 50. Column 50 separates the product cumene from yet higher boiling effluent components. Column 50 is a trayed column, designed to provide cumene at a desired degree of purity The cumene products are taken overhead by a product line 44 while the heavier components are transferred to a heavy alkylate column by line 46.

Heavy alkylate column 60 is designed to recover di- and tri-isopropyl benzenes and reject heavier undesirable by-products of the alkylation and transalkylation reactions. Such by-products include condensed benzene ring compounds and aromatics substituted with propylene condensation products. These heavy products are taken from the bottom of column 60 through a line 48 and removed from the process. Di-isopropyl benzene and tri-isopropyl benzene are taken overhead by line 50 and combined with benzene from line 36 in a transfer line 52. The benzene and poly-substituted benzenes make up the feed inputs to the transalkylation zone 24.

After any appropriate heat exchange, the contents of line 52 enter the transalkylation zone 24 at a temperature of 220° C. and a pressure of 35 atmospheres. The reactants flow upwardly and contact a crystalline alumina silicate catalyst of the preferred composition as hereinbefore described. Reactants flow upward in a quantity sufficient to provide an LHSV in a range of 0.5 $hr^{-1}$ to 5.0 $hr^{-1}$. Reaction products and reactants comprising benzene, isopropyl benzene, di- and tri-propyl benzenes plus minor amounts of other heavy alkylate components enter collection zone 22 where they are combined with the reaction zone effluent in the manner hereinbefore described.

What is claimed is:

1. A process for the production of alkylaromatic hydrocarbons which comprises contacting feed aromatic hydrocarbons and acyclic hydrocarbons in an alkylation reaction zone maintained at conditions to promote alkylation and recovering a reaction zone effluent comprising unconverted feed aromatic hydrocarbons and product aromatic hydrocarbons; wherein at least a portion of said unconverted feed aromatic hydrocarbons are recovered by:

(a) combining the reaction zone effluent with a working fluid upstream of any separation in an amount such that said working fluid equals at least 2 wt. % of said reaction zone effluent to obtain a combined effluent stream, said working fluid having a substantially lower boiling point than said feed aromatic hydrocarbons;

(b) maintaining said combined effluent stream at a temperature sufficient to vaporize at least a portion of said working fluid;

(c) passing said combined effluent stream to a flash separator and recovering an overhead stream comprising the working fluid and at least a portion of said unconverted feed aromatic hydrocarbons and a bottoms stream comprising said product aromatic hydrocarbons;

(d) passing said overhead stream from said flash separator to a separation zone and recovering a bottoms recycle stream comprising said unconverted feed aromatic hydrocarbons and an overhead stream comprising said working fluid; and (e) returning at least a portion of the recovered recycle stream to said alkylation reaction zone.

2. The process of claim 1 wherein said feed aromatic hydrocarbons comprise benzene and said product aromatic hydrocarbons comprise isopropyl benzene and said working fluid comprises acyclic hydrocarbons.

* * * * *